United States Patent [19]
Ganz et al.

[11] Patent Number: 5,810,807
[45] Date of Patent: Sep. 22, 1998

[54] SPHINCTEROTOME WITH DEFLECTABLE CUTTING PLANE AND METHOD OF USING THE SAME

[76] Inventors: Robert A. Ganz, 1431 Lakeview Ave., Minneapolis, Minn. 55416; Jonathan Kagan, 5112 Russell Ave. So., Minneapolis, Minn. 55410; Ricci D. Smelser, P.O. Box 609, 26 S. Oaks, Maple Lake, Minn. 55358; Brian D. Zelickson, 2764 Drew Ave. So., Minneapolis, Minn. 55416; Robert D. Mackie, 25 Pheasant La., North Oaks, Minn. 55127

[21] Appl. No.: 732,092

[22] Filed: Oct. 15, 1996

Related U.S. Application Data

[60] Provisional application No. 60/018,142 May 22, 1996.
[51] Int. Cl.⁶ .................................................. A61B 17/36
[52] U.S. Cl. ............................................. 606/47; 606/113
[58] Field of Search ....................... 606/47, 113; 600/104, 600/105, 106; 604/95

[56] References Cited

U.S. PATENT DOCUMENTS

| | | | |
|---|---|---|---|
| 1,741,740 | 12/1929 | Sederholm et al. | 606/47 |
| 3,605,725 | 9/1971 | Bentov | 128/2.05 R |
| 4,326,530 | 4/1982 | Fleury, Jr. | 128/303.14 |
| 4,586,923 | 5/1986 | Gould et al. | 604/95 |
| 4,643,187 | 2/1987 | Okada | 128/303.15 |
| 4,685,457 | 8/1987 | Donenfeld | 128/207.14 |
| 4,753,223 | 6/1988 | Bremer | 128/4 |
| 5,013,312 | 5/1991 | Parins et al. | 606/37 |
| 5,024,617 | 6/1991 | Karpiel | 606/47 |
| 5,035,696 | 7/1991 | Rydell | 606/47 |
| 5,090,956 | 2/1992 | McCoy | 604/95 |
| 5,201,732 | 4/1993 | Parins et al. | 606/47 |
| 5,273,026 | 12/1993 | Wilk | 128/20 |
| 5,273,535 | 12/1993 | Edwards et al. | 604/95 |
| 5,318,525 | 6/1994 | West et al. | 604/95 |
| 5,334,168 | 8/1994 | Hemmer | 604/281 |
| 5,383,852 | 1/1995 | Stevens-Wright | 604/95 |
| 5,398,670 | 3/1995 | Ortiz et al. | 128/6 |
| 5,431,168 | 7/1995 | Webster, Jr. | 128/658 |
| 5,441,483 | 8/1995 | Avitall | 604/95 |
| 5,484,407 | 1/1996 | Osypka | 604/95 |

OTHER PUBLICATIONS

V.K. Paruskar et al, Tip Deflecting Cannula; A Novel Approach to Facilitate Difficult Bile Duct Cannulation, Abstract #2255 *Proc. Dig. Disease Week*, San Francisco, CA, May, 1996.

*Primary Examiner*—Michael H. Thaler
*Attorney, Agent, or Firm*—Joseph F. Breimayer

[57] ABSTRACT

A sphincterotome adapted to be used in the lumen of an endoscope for cutting a sphincter in a patient's body using a cutting wire energized by an electrosurgical unit. The sphincterotome has a distal end segment and cutting plane orienting mechanism extending through the length of a sphincterotome tubular body between a handle assembly at the proximal end of the sphincterotome body and a distal end segment thereof for shifting the cutting plane laterally with respect to the longitudinal axis of the sphincterotome tubular body exiting the endoscope lumen. The lateral shift is in at least one lateral direction from an un-shifted position of the cutting plane with respect to the longitudinal axis whereby in use during a sphincterotomy, the cutting wire may be oriented into alignment with a particular feature of the sphincter, e.g. the twelve o'clock position of the sphincter of Oddi and papilla of Vater, without having to reposition the endoscope and/or withdraw and reposition the sphincterotome in the endoscope lumen.

23 Claims, 9 Drawing Sheets

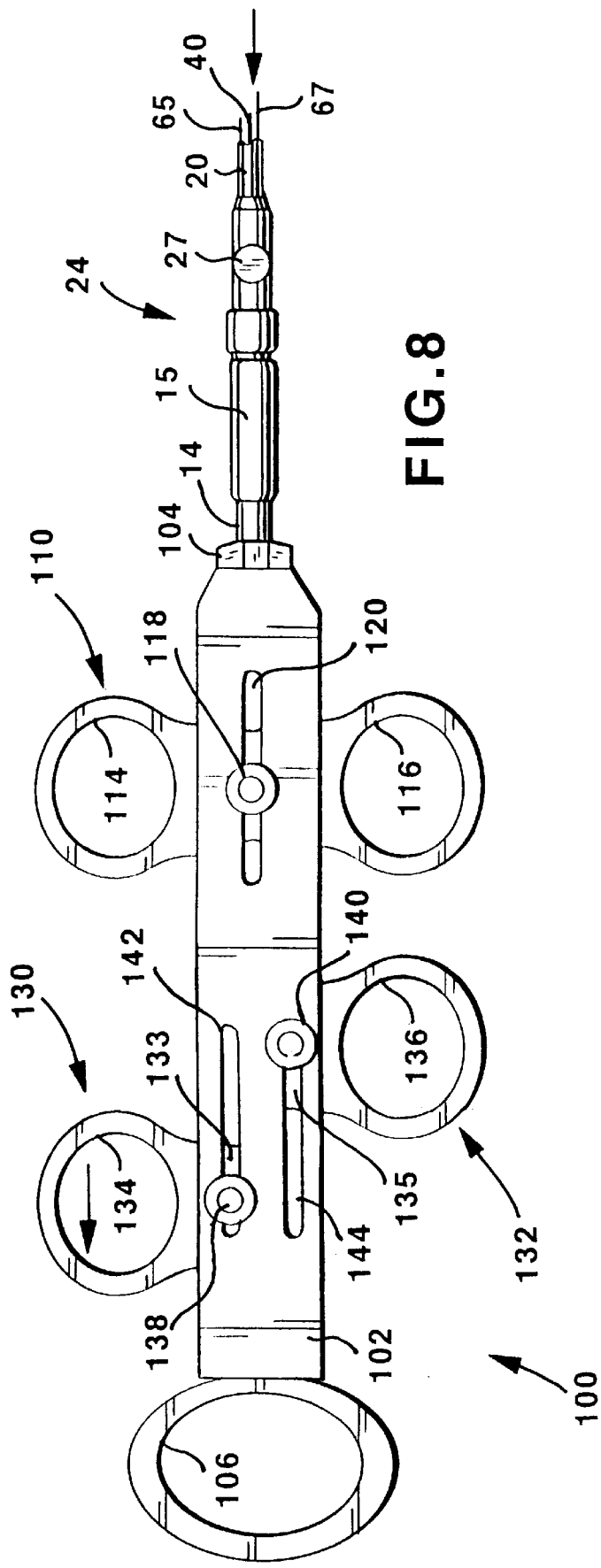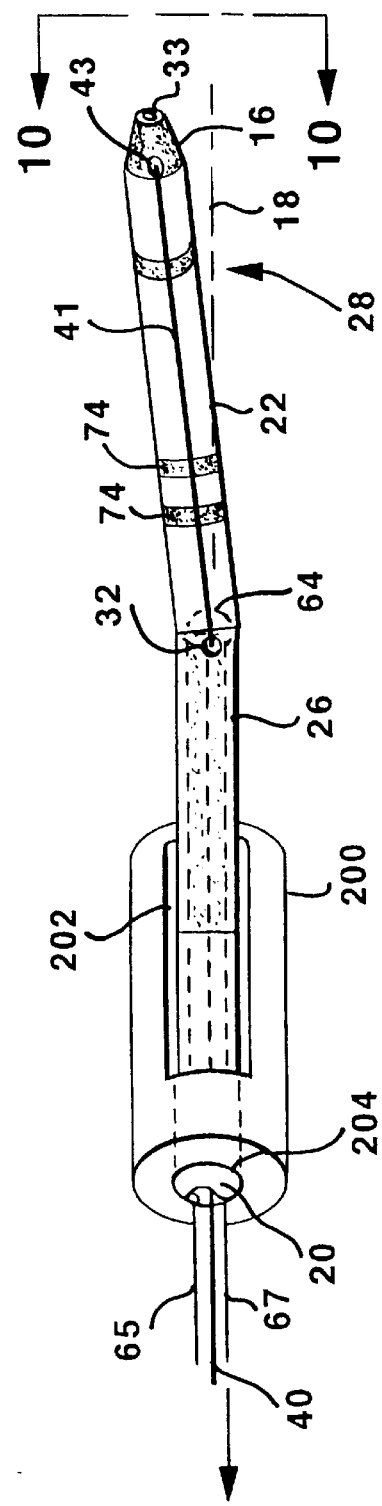

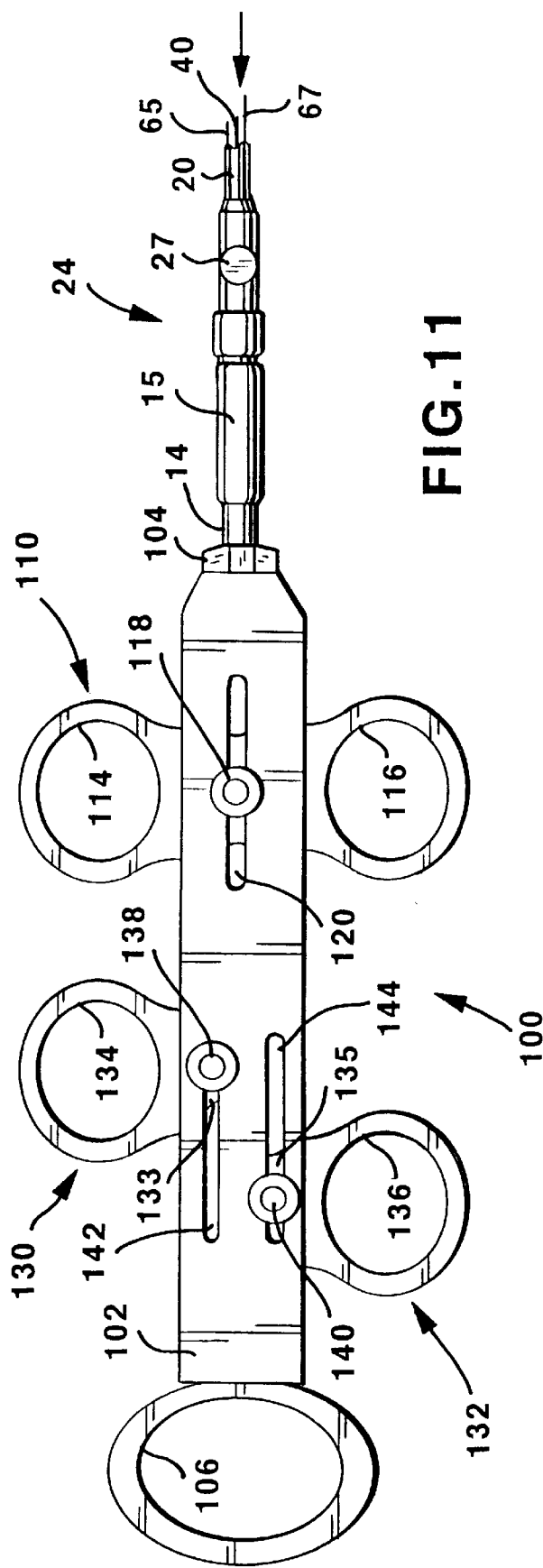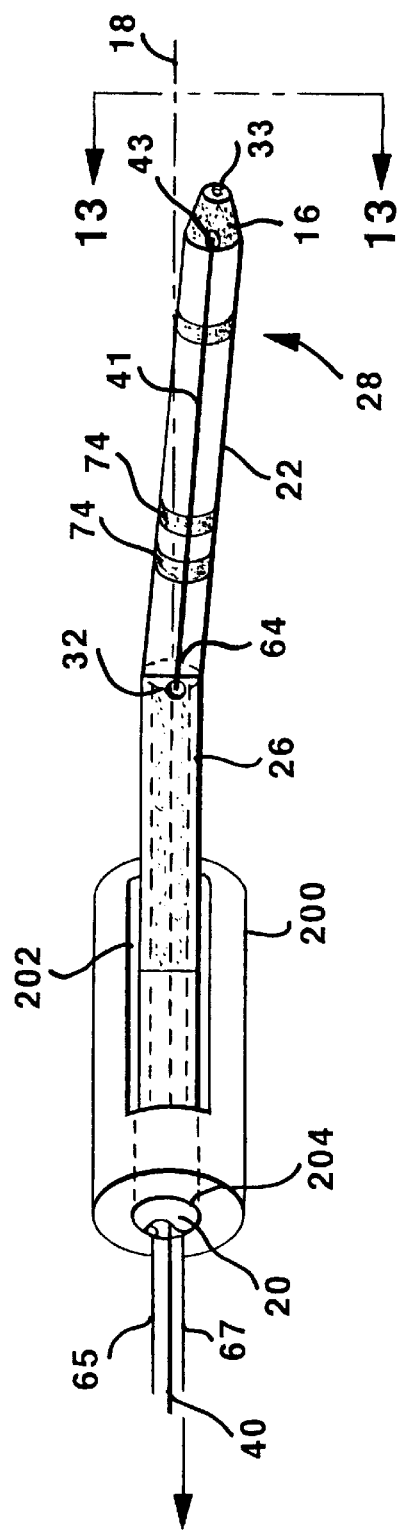
FIG. 11
FIG. 12

SPHINCTEROTOME WITH DEFLECTABLE CUTTING PLANE AND METHOD OF USING THE SAME

This application claims the benefit of U.S. Provisional Application No. 60/18,142 filed May 22, 1996.

FIELD OF THE INVENTION

The present invention relates generally to sphincterotomy, and more specifically to sphincterotomes having a distal end segment and cutting plane that may be oriented through a proximal manipulation within an angular range into a patient's sphincter opening to provide controlled cutting of the sphincter.

BACKGROUND OF THE INVENTION

In endoscopic sphincterotomy, an electrosurgical instrument, known as a sphincterotome or papillotome, is used in conjunction with an endoscope to provide surgical cutting of a sphincter at a site inside a patient's body. For example, the Sphincter of Oddi opens into the duodenum at the Papilla of Vater, with the common bile duct and the pancreatic duct merging into a common chapel, the Ampulla of Vater. A sphincterotome or papillotome (hereafter referred to as a sphincterotome for convenience) may be used to partially cut open the Papilla of Vater to enlarge it to allow passage of common bile duct stones obstructing the bile duct. As stated in U.S. Pat. Nos. 5,024,617 and 5,035,696, when gallstones form in the gallbladder and achieve a size too large to pass through the common bile duct into the duodenum, a biliary colic may result site of the blockage is the sphincter of Oddi, a less traumatic procedure referred to as "endoscopic retrograde sphincterotomy" (ERS) may be used to cut the sphincter sufficiently to permit even large size gallstones lodged at that site to pass into the duodenum.

The ERS procedure is preceded typically by an "endoscopic retrograde cholangiopancreatography" (ERCP) procedure, wherein a side-viewing endoscope is passed through the esophagus into the stomach and from there through the pyloric sphincter into the duodenum where the site is illuminated. While viewing through a fiber optic bundle extending within the endoscope, the distal end of the endoscope is made to approach the papilla of Vater. When the distal end is positioned, an ERCP cannula is passed through the endoscope, out the side port and then through the sphincter of Oddi into the common bile duct. In order to advance the cannula into the papilla of Vater, a guide wire may first be advanced by the same route into the common bile duct while being viewed through the fiberoptic bundle, and the cannula may then be advanced over the guide wire. When the cannula is so positioned, a suitable contrast fluid may be injected through the catheter lumen so that any gallstones displacing the fluid can be viewed through fluoroscopy and their size evaluated by the physician. The ERCP procedure may be terminated and the patient at that point become an abdominal surgery candidate if a gallstone is deemed to be too large to pass through the sphincter of Oddi even after the sphincter is enlarged in a sphincterotomy.

The ERS procedure is commenced if the sizes of the gallstones are judged to be sufficiently small to pass the enlarged sphincter. The ERCP cannula is removed, and a sphincterotome having a tapered distal tip is advanced through the lumen of the endoscope and out the side port thereof and through the sphincter of Oddi. Certain sphincterotomes are advanced over the cannula guide wire that is left in position, and others may be advanced without a guidewire.

A simple sphincterotome body is formed of a flexible, catheter-like tubular sphincterotome member sized to fit within the endoscope lumen and with a cutting wire lumen formed therein extending from the proximal end thereof to a side wall opening proximal to the distal end thereof A proximal portion of the cutting wire extends through the cutting wire lumen, and a distal portion passes out the side wall opening and extends along the tubular member to a point of attachment of the distal cutting wire end thereof adjacent to but typically spaced from the distal tip of the tubular member. The tubular member distal end segment may be tapered to its distal end, and may have distance markings and radiopaque bands along its length. The cutting wire lumen may also extend to a distal tip opening at the distal end of the tubular member and be used as a guide wire lumen and/or to dispense radiopaque contrast medium Alternatively, one or more separate lumens and distal end exit openings may be provided and employed for these purposes. The distal cutting wire portion and the distal segment of the tubular member form a distal section of the sphincterotome body.

A handle assembly at the proximal end of the sphincterotome body is provided for advancing and retracting the tubular member forward through and back into the endoscope lumen, over the guide wire (if any) and into and out of the sphincter. The handle assembly also includes a mechanism coupled with the proximal end of the cutting wire that is manipulatable between a slack position allowing the cutting wire to be slack within the cutting wire lumen and alongside the side wall of the distal end segment during introduction of the distal end segment through the sphincter and an operative position retracting and applying tension to the cutting wire to separate the cutting wire from the side wall of the distal end segment after the distal end section is advanced out the side wall opening of the endoscope. When the mechanism is manipulated into the operative position, the tension on the cutting wire forms about a 90° bend in the distal end segment, thereby displacing the bend and cutting wire apart in a cutting plane with the bend in the distal end segment.

The cutting wire is also electrically connected to an electro surgical, radio frequency energy generator that is actuable by the physician to electrically heat the cutting wire to a temperature that cauterizes the tissue through diathermy currents conducted through the tissue contacted by the cutting wire. Either a bipolar electrode is located on or near the distal end segment or a remote skin contacting electrode is employed as a return electrode for the diathermy current.

For safe, effective results, the sphincterotomy incision must be precisely located. The anatomical structures of the papilla of Vater and the sphincter of Oddi are observed through the endoscope to orient the side opening of the endoscope toward them When the papilla is viewed anteriorly, the common bile duct courses to the left and cephalid, the pancreatic bile duct to the right and horizontally. These guidelines are used in the ERS procedure to successfully cannulate the common bile duct with the distal end segment of the sphincterotome. Then, the cutting wire must be positioned to ensure that it incises into the intramural common bile duct at a twelve o'clock position, thereby avoiding trauma to the duodenal wall or the pancreas.

In use, as shown in FIGS. 7 and 8 of the above-referenced '617 patent, incorporated herein by reference, the physician advances the straight distal end section of the sphincterotome body out through the endoscope lumen and into the common bile duct as described above. Contrast fluid may be injected through a port on the handle assembly communicating with an appropriate lumen and out the distal exit port of the distal end segment to confirm that it is positioned in the common bile duct. Then, the substantially straight distal end section is retracted into a bend until the distal portion of the cutting wire exiting the side exit port and/or a particular marking band can be seen through the endoscope fiber optic cable indicating the length of the incision to be made. At this point, the physician must determine that the cutting plane to be formed when the cutting wire is retracted will result in the cutting wire bearing against the sphincter opening at the desired twelve o'clock position through the length of the incision.

As described above, certain sphincterotomes are designed to be advanced over a guidewire whereas others, e.g. that shown in the above-incorporated '617 patent, are not. In the former case, the distal end segment of the sphincterotome body and the exposed cutting wire portion may be advanced over the guidewire to position at least a distal tip portion thereof into the sphincter opening before forming the cutting plane and determining if the desired orientation has been achieved. In the latter case, it is necessary to rely on precise orientation of the endoscope side exit port to common bile duct leading to the sphincter opening. At times it is difficult to achieve this orientation and to direct the distal tip portion into the sphincter opening. Moreover, at times it is preferable to not use a guidewire or to insert the guidewire into the sphincter opening.

Assuming that the distal tip portion is placed correctly into the sphincter opening, and when the physician judges that the correct orientation of the cutting plane to the twelve o'clock position can be attained, the cutting wire is retracted further to form the cutting plane with the resulting bend in the distal end section. The electrosurgical unit is energized to deliver RF energy to the cutting wire to heat it and begin incising the papilla, intramural duct wall and sphincter muscle to a desired depth to effectively allow the sphincter opening to expand and pass gallstones of a size too large to pass through the sphincter normally. The depth and length of the incision must be carefully estimated in advance and controlled in the process while viewing the site through the endoscope. The resulting size of the opening of the sphincter and bile duct along the length of the incision may be checked by withdrawing the sphincterotome and inserting a balloon catheter through the endoscope lumen, into the common bile duct past the incision, and inflating it to a size that passes through the opening. The ERS procedure may then be repeated or terminated depending on the results.

The distal end segment of the tubular member and the associated distal end portion of the cutting wire may exit the endoscope side exit opening at a radial angle that does not quite precisely orient the cutting plane in alignment with the twelve o'clock position. The sphincterotome body distal section may also be exiting the endoscope distal opening at an incorrect angle to the sphincter opening. Or, it may be difficult to align the endoscope distal opening at an optimum orientation to the sphincter opening. The tubular member of the sphincterotome fits snugly within the endoscope lumen, and the endoscope may typically follow a twisted path in the body to the site. As a result, the friction of the sphincterotome body outer wall against the endoscope lumen inhibits rotation of the sphincterotome body with respect to the endoscope lumen by manipulation of the handle assembly precisely enough to correct the mis-alignment. A 1:1 torque transfer and twisting motion down the length of the tubular member is prevented by binding within the endoscope lumen. It is therefore necessary to attempt to reposition the endoscope and the sphincterotome several times to obtain the desired orientation. It may be necessary to fully retract the sphincterotome tubular body out of the endoscope lumen, insert it again at a slightly different angle, and to repeat the steps of the ERS procedure several times before an acceptable orientation is achieved. It may also be necessary to reposition the endoscope first. The position of the patient's body on the operating table may also have to be shifted. A great deal of patience and experience is required to correctly orient the cutting plane to the twelve o'clock position.

As noted in the above-incorporated '617 patent, a serious mortality rate exists with the ERS procedure attributed at least in part to improper orientation of the cutting wire and cutting plane to the twelve o'clock position. If not properly oriented, the cutting wire may sever the retroduodenal artery, perforate the duodenum, or cause pancreatitus if the pancreatic duct is cut. A sphincterotome is disclosed in the '617 patent having a full length, rectangular cross-section, reinforcing wire incorporated into the tubular member for enhancing the rigidity of the cutting plane. The focus of the '617 patent appears to be in avoiding the lateral bending of the distal end of the tubular member under the tension of the retracted cutting wire and/or preventing the inadvertent twisting of the sphincterotome tubular body as it is advanced down the length of the endoscope lumen. Reinforcement of the distal end segment of the tubular member by the coiled wire, return electrode is also present in the above-referenced '696 patent. In both cases, care must still be taken to ensure that the distal end opening of the endoscope is initially positioned in relation to the sphincter with a high degree of precision to achieve the orientation of the cutting plane to the twelve o'clock position.

SUMMARY OF THE INVENTION

Accordingly, it is an object of the present invention to provide an improved sphincterotome to avoid trial and error repositioning in the orientation of the endoscope and the cutting wire in a cutting plane to a particular feature of a sphincter opening.

It is a further object of the present invention to provide an improved sphincterotome that may be manipulated from its proximal handle to compensate for the inability to precisely orient the endoscope with respect to a sphincter.

It is a still further object of the invention to provide a method and apparatus for providing a variable angular orientation of the cutting wire and cutting plane to the feature of the sphincter opening within a range of angular orientations from a starting sub-optimal orientation.

These and other objects of the present invention are realized in an improvement to the above described sphincterotome and an improved method of use thereof providing the capability of deflecting a distal end segment of the sphincterotome body and the exposed cutting wire portion extending alongside it through the use of deflecting means extending through the length of a sphincterotome body that may be manipulated at the proximal end to aid in positioning the distal end segment and cutting wire portion into a desired orientation with the sphincter opening. In a first aspect of the invention, the deflecting means may be employed to attain the desired orientation to and advance of the distal tip of the sphincterotome body into the sphincter opening with the exposed cutting wire portion relatively slack alongside the distal end segment. Then, the cutting plane may be formed by retraction of the distal cutting wire portion and the deflecting means may be manipulated to orient the cutting plane to a specific feature of the sphincter to allow the exposed and retracted cutting wire portion to cut the sphincter when it is energized.

In a preferred embodiment, the deflecting means extends between a handle assembly at the proximal end of the sphincterotome body and the distal end segment thereof for shifting the cutting plane laterally with respect to the longitudinal axis of the sphincterotome tubular body exiting the endoscope lumen. The lateral shift is in at least one lateral direction from an un-shifted position of the cutting plane with respect to the longitudinal axis whereby in use during a sphincterotomy, the cutting wire may be oriented into alignment with a particular feature of the sphincter, e.g. the twelve o'clock position of the sphincter of Oddi and papilla of Vater, without having to reposition the endoscope and/or withdraw and reposition the sphincterotome in the endoscope lumen.

BRIEF DESCRIPTION OF THE DRAWINGS

Other objects, advantages and features of the present invention will be readily appreciated as the same becomes better understood by reference to the following detailed description when considered in connection with the accompanying drawings (which are not necessarily to scale), in which like reference numerals designate like parts throughout the figures thereof and wherein:

FIG. 8 is a top plan view of the sphincterotome handle with the left pull wire retracting and tensioning member in a retracted position for deflecting the cutting plane to the left;

FIG. 9 is an enlarged partial top view of the distal end portion of the sphincterotome tubular member in the retracted position of FIGS. 5 and 8 exiting the side exit opening of an endoscope;

FIG. 11 is a top plan view of the sphincterotome handle with the right pull wire retracting and tensioning member in a retracted position for deflecting the cutting plane to the right;

FIG. 12 is an enlarged partial top view of the distal end portion of the sphincterotome tubular member in the retracted position of FIGS. 5 and 11 exiting the side exit opening of an endoscope.

DETAILED DESCRIPTION OF THE PREFERRED EMBODIMENTS

Figure 1:
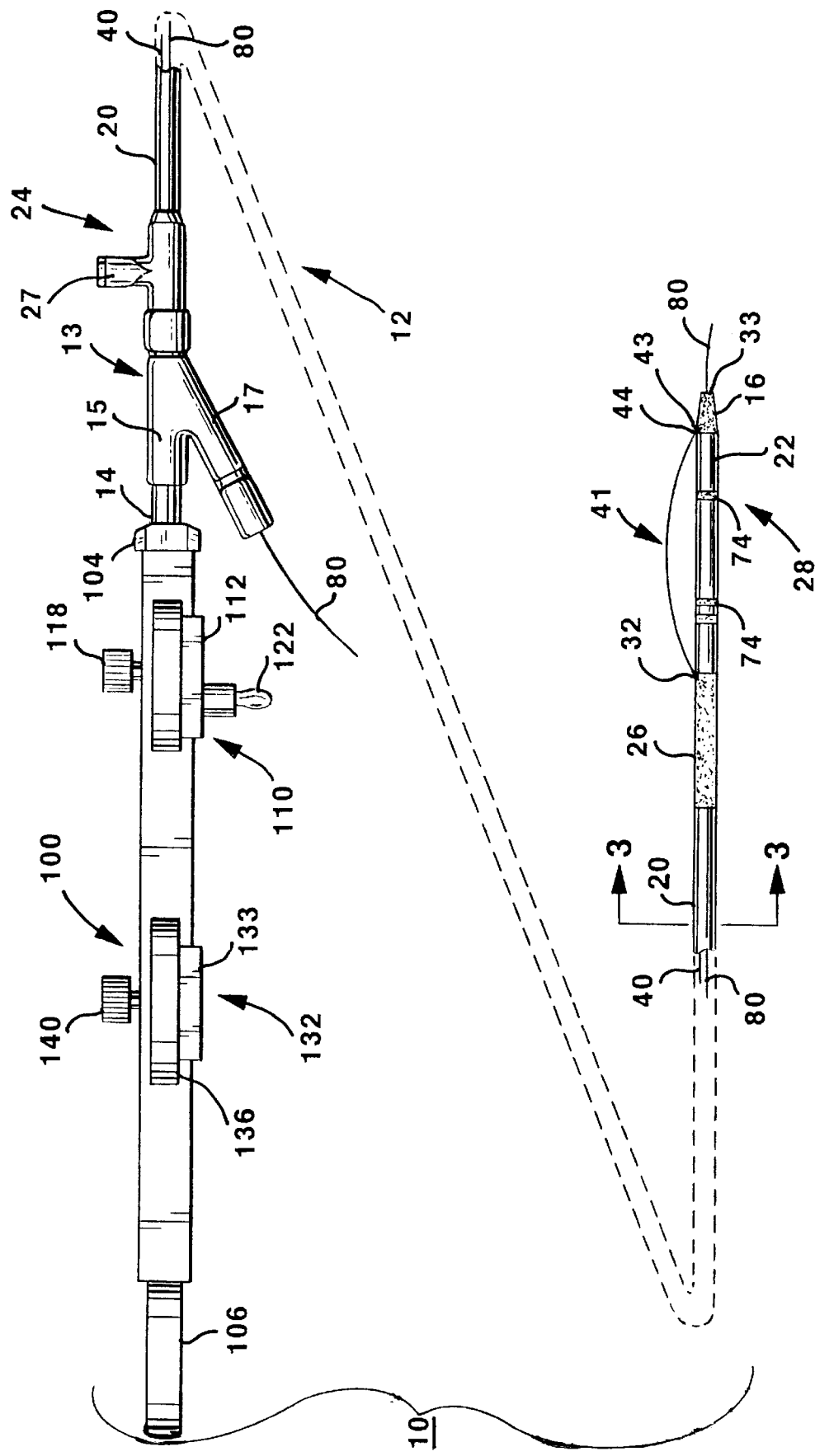
FIG. 1 is a side plan view of the sphincterotome of a preferred embodiment of the present invention in a slack position wherein the distal section of the sphincterotome body is substantially straight.

The preferred embodiment of the present invention is realized in a sphincterotome 10 depicted in the drawings in relation to an endoscope 200 for performing an ERS procedure of the type described above, although it may be used for similar sphincterotomy procedures of other sphincters or restricted passageways in the body. The sphincterotome 10 is formed of a manipulatable handle assembly 100 and an elongated sphincterotome body 12 having a proximal end 14 and a distal end 16 and formed of a flexible tubular member 20 with a side wall 22 enclosing four lumens shown in FIG. 3 of a predetermined outer diameter adapted to fit within an introduction lumen 204 of an endoscope 200. Although the preferred embodiment illustrated in the drawings and described below includes a guidewire lumen, it will be understood that the invention may be practiced in sphincterotomes that do not have guidewire lumens and/or are not advanced into the sphincter opening over a guidewire or through an introducer lumen already extending into the opening.

Figure 2:
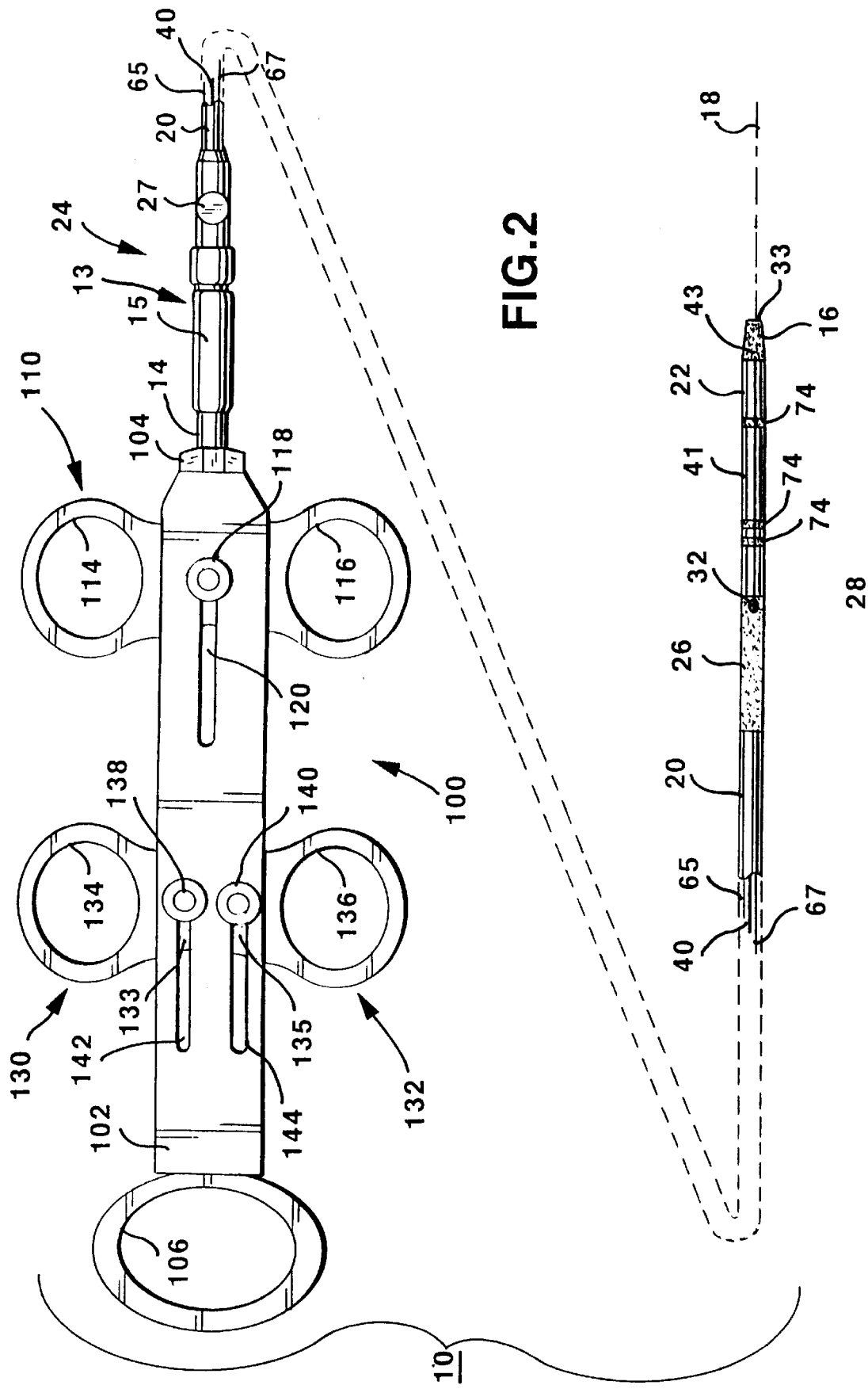
FIG. 2 is a top plan view of the sphincterotome of a preferred embodiment of the present invention in the slack position of FIG. 1.
Figure 3:
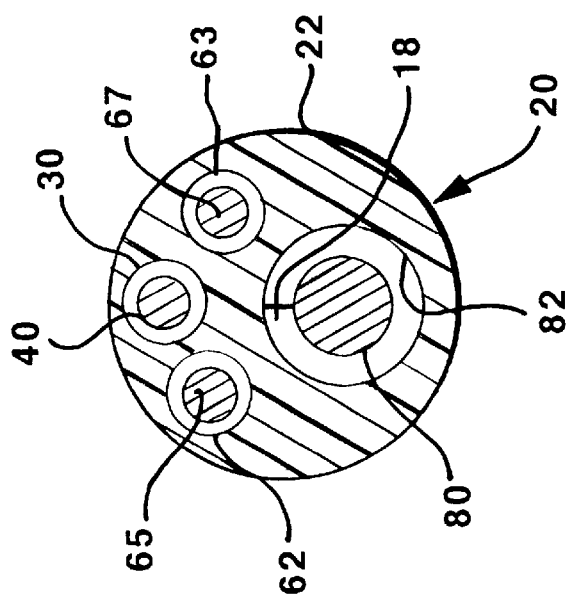
FIG. 3 is a cross-section view of the tubular member of the sphincterotome body of FIGS. 1 and 2.

Turning to FIGS. 1–3, the flexible tubular member 20 is of a length extending through a proximal end segment 24 to a junction 26 with a distal end segment 28. An enlarged Y-connecting member 13 has a main branch 15 receiving the proximal end 14 and a side branch 17 with a side branch guidewire lumen therein for receiving a guidewire 80. The side branch guidewire lumen is in communication with the primary guidewire lumen 82 of the tubular member 20. A seal of a type well known in the art may be formed in the side branch guidewire lumen that is penetrable by the guidewire 80 and prevents backflow and loss of contrast media injected into the primary guidewire lumen 82.

The injection of contrast media into the primary guidewire lumen 82 is effected through an injection port 27 of a type well known in the art extending outward from the main branch 15 and having an injection lumen in fluid communication with the primary guidewire lumen 82. In an alternative embodiment intended for introduction without the assistance of a guidewire 80, the side branch 17 may be eliminated.

In the cross-section view of the tubular member 20 shown in FIG. 3, the guidewire and contrast fluid injection lumen 82 is shown in relation to a further single cutting wire lumen 30, for a unipolar sphincterotome, and left and right pull wire lumens 62 and 63 formed in the tubular member 20 in accordance with the present invention. The flexible tubular member 20 may be formed of a transparent polymer, e.g. polyurethane, polyethylene, tetrafluoroethylene, polytetrafluoroethylene, perfluoalkoxl, fluorinated ethylene propylene, or the like, with at least one cutting wire lumen 30 formed therein. The cutting wire lumen 30 and the pull wire lumens 62 and 63 extend from the proximal end 14 through the proximal and distal end segments 24 and 28 to a point near the tubular member distal end 16. A proximal side wall opening or exit port 32 is formed at the junction 26 of the proximal end segment 24 with the distal end segment 28 as shown in FIGS. 1 and 2. A distal side wall exit port 43 is formed in the side of the distal end 16 for receiving the distal end of the cutting wire 40. The primary guidewire lumen 82 extends the length of the tubular member 20 and terminates in a distal exit port 33 in tip 16 so that the sphincterotome body can be advanced over a guidewire 80 and/or contrast fluid may be delivered as described above.

The axes of the cutting wire lumen 30 and pull wire lumens 62 and 63 are offset radially from the central longitudinal axis 18 of the generally circular tubular member 20 and from one another. The primary guidewire lumen 82 and the cutting wire lumen 30 are centered on a diametric line across the cross section of the tubular member 20. The pull wire lumens 62 and 63 extend generally along either side of the cutting wire lumen 30 within an arc of less than 180° measured from the longitudinal axis 18. The sphincterotome cutting wire 40 and left and right pull wires 65 and 67 are loosely contained in and extend through the respective lumens 30, 62 and 63 and extend proximally from proximal end openings of the tubular member 20 into the handle assembly 100. The guidewire 80 is also received within guidewire lumen 82 with sufficient clearance to allow advancement of the tubular member 20 over it.

Figure 4:
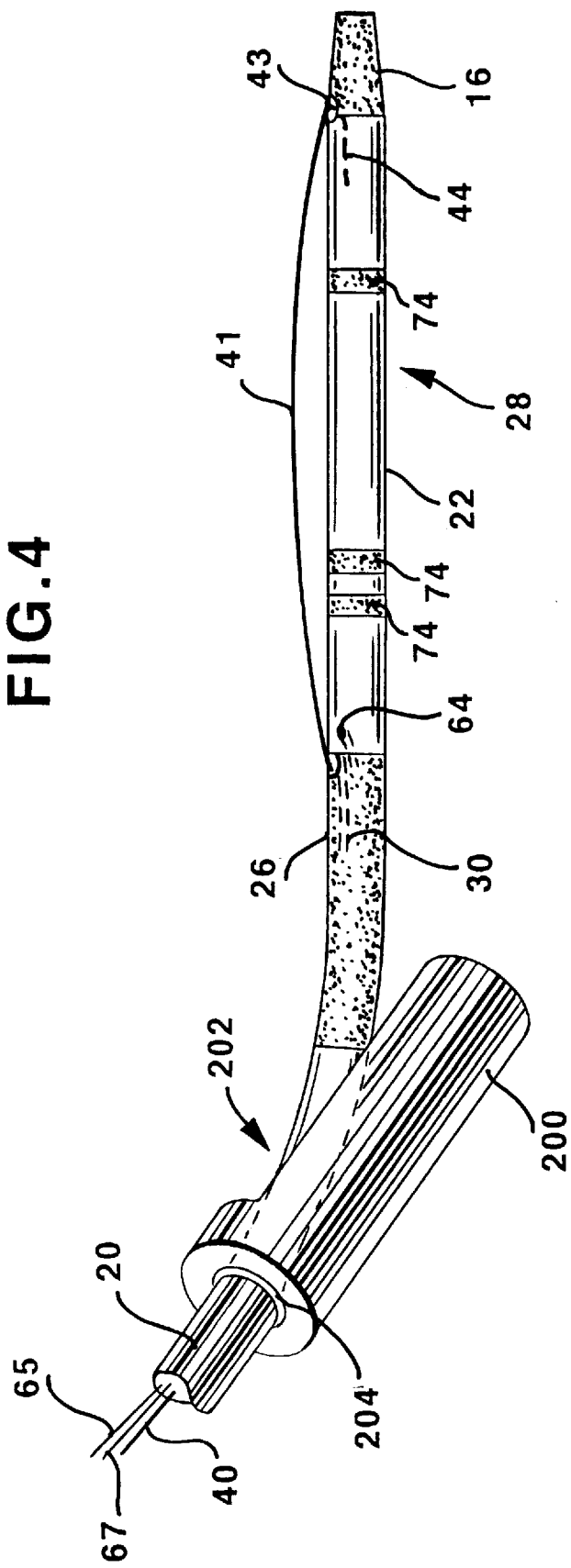
FIG. 4 is an enlarged partial side view of the distal end portion of the sphincterotome tubular member in the relaxed position of FIG. 1 and exiting the side exit opening of an endoscope.

The distal end segment 28 and the relatively slack distal exposed cutting wire portion 41 terminating in distal cutting wire end 44 are shown exiting from the distal, side exit port 202 of a conventional endoscope 204 in the enlarged partial side view of FIG. 4. The proximal portion of the tubular member 20 is restrained within the endoscope lumen 204 terminating in the side exit port 202 in a manner shown in FIGS. 6 and 7 of the '617 patent. The endoscope 200 maybe of any of the known types and other details of its construction are omitted. The endoscope lumen 204 restrains any movement of the tubular member 20 within the endoscope lumen 204 laterally to the axis of the endoscope lumen 204. The cutting wire 40 in cutting wire lumen 30 and the right and left pull wires 63 and 65 are also shown in FIG. 4, whereas the guidewire 80 is omitted for clarity. As described below, a common termination 64 of the pull wire lumens 62 and 63 providing a common attachment point for the distal ends of the pull wires 65 and 67 is also represented in FIG. 4.

As also shown in FIGS. 1 and 2, the distal tip 16 of the distal end segment 28 is preferably tapered to the end opening 33 and maybe formed of a radiopaque material. The junction 26 may be marked by a wide band of radiopaque material. A plurality of distance markers 74 may be formed along the distal end segment 28 for the physician to use in judging how far to withdraw the distal end segment 28 prior to retracting the cutting wire 40 and making the incision.

Returning to FIGS. 1 and 2, the handle assembly 100 comprises an elongated handle body 102 having a coupling 104 for connection with the sphincterotome body proximal end 14 and for receiving the proximal ends of the cutting wire 40 and the pull wires 65, 67 therein. A thumb receiving loop 106 is fixedly attached to the handle body 102. A cutting wire retracting and tensioning member 110 is formed of a bridge member 112 connecting a pair of finger engaging loops 114 and 116 extending laterally of the elongated handle body 102. The cutting wire retracting and tensioning member 110 is provided with a range of motion along the length of the elongated handle body 102 defined by an elongated opening 120 through the elongated handle body 102 cooperating with the thumb screw 118. The thumb screw 118 may be tightened to hold the bridge member 112 against the lower surface of the handle body 102 at any position along the elongated opening to define the degree of bending of the distal end segment 28. The bridge member 112 is mechanically attached to the proximal end of the cutting wire 40 and also supports an electrical connector pin or terminal 122 that is electrically connected to the proximal end of the cutting wire 40 in a manner well known in the art. A cable leading to an electrosurgical RF generator may be connected to the terminal 122, and the electrical connection may be maintained at any position of the elongated handle body 102.

The cutting wire tensioning and retracting member 110 at the proximal end 14 of the sphincterotome body 12 and the proximal cutting wire end is manipulatable by the physician to a slack position as shown in FIGS. 1 and 2, allowing a proximal cutting wire portion of the cutting wire 40 to be relatively slack within the cutting wire lumen 30 and a distal cutting wire portion 41 to lie alongside the side wall 22 of the distal end segment 28 during introduction of the distal end segment 28 to a body site for performing a sphincterotomy. Then, the physician may use the finger engaging loops 114, 116 and the thumb engaging loop 106 to retract and apply tension to the cutting wire 40 to separate the distal cutting wire portion 41 from the side wall 22 of the distal end segment 28 and to form a bend in the distal end segment 28 in a cutting plane for performing a sphincterotomy.

It should be noted that in the preferred embodiment, the cutting wire 40 is preferably of a single piece including the distal exposed cutting wire portion 41 and provides the means for both conduct the electrosurgical current and conveying the retraction force to the distal cutting wire portion 41 thereof. Of course, the cutting wire 40 and the distal cutting wire portion 41 may be construed to include separate wires or other structures for effecting the energization and retraction of the distal cutting wire portion 41.

The handle assembly 100 also includes left and right pull wire tensioning and retracting members 130 and 132 formed of left and right finger engaging loops 134 and 136, respectively, extending laterally from the sides of the elongated handle body 102 that are constructed in a manner similar to cutting wire tensioning and retracting member 110 but operate independently from one another. Brackets 133 and 135 extend from the finger engaging loops 134 and 136, respectively, below the lower surface of the elongated handle body 102 to guide proximal and distal displacement of the pull wire tensioning and retracting members 130 and 132 along elongated openings 142 and 144, respectively. The pull wire tensioning and retracting members 130 and 132 are provided with ranges of motion along the length of the elongated handle body 102 defined by the elongated openings 142 and 144 through the elongated handle body 102 in cooperation with thumb screws 138 and 140, respectively, threaded into brackets 133 and 135. The thumb screws 138 and 140 maybe tightened to hold the respective bracket 133 and 135 against the lower surface of the handle body 102 at any position along the length of the elongated openings 142 and 144. The brackets are mechanically attached to the proximal ends of the pull wires 65 and 67, respectively, internally to elongated handle body 102 in a manner well known in the art.

Although the pull wire tensioning and retracting members 130 and 132 are shown proximal to the cutting wire tensioning and retracting member 110 along handle body 102, it will be understood that the positions may be reversed. It will also be understood that the slide action and tightening mechanism provided by the pull wire tensioning and retracting members 130 and 132 and the cutting wire tensioning and retracting member 110 and their attachment to the proximal ends of the pull wires 65 and 67 and the cutting wire 40 may be effected in many ways.

The proximal and distal end segments 24 and 28 are substantially straight when unrestrained as shown in FIGS. 1, 2 and 4 but have bending flexibility allowing bends to be formed therein so that the tubular member 20 may be advanced over guidewire 80 and through the lumen and side exit opening of an endoscope (not shown). The sphincterotome cutting wire 40 has its proximal cutting wire end coupled to the cutting wire retracting and tensioning member 110 as described above and its cutting wire distal end 44 fastened into the distal tip 16. The cutting wire distal end 44 is inserted through the distal side wall exit port 43 back into the lumen 40 for a certain distance, and adhesive may be used to hold it in place. The proximal cutting wire portion extends through the cutting wire lumen 30, and a distal, exposed cutting wire portion 41 exiting through the side wall exit port 32 and extending alongside the side wall 22 of the distal end segment 28. The distal end segment 28 and the distal cutting wire portion 41 comprise the distal end section of the sphincterotome body 12.

Figure 5:
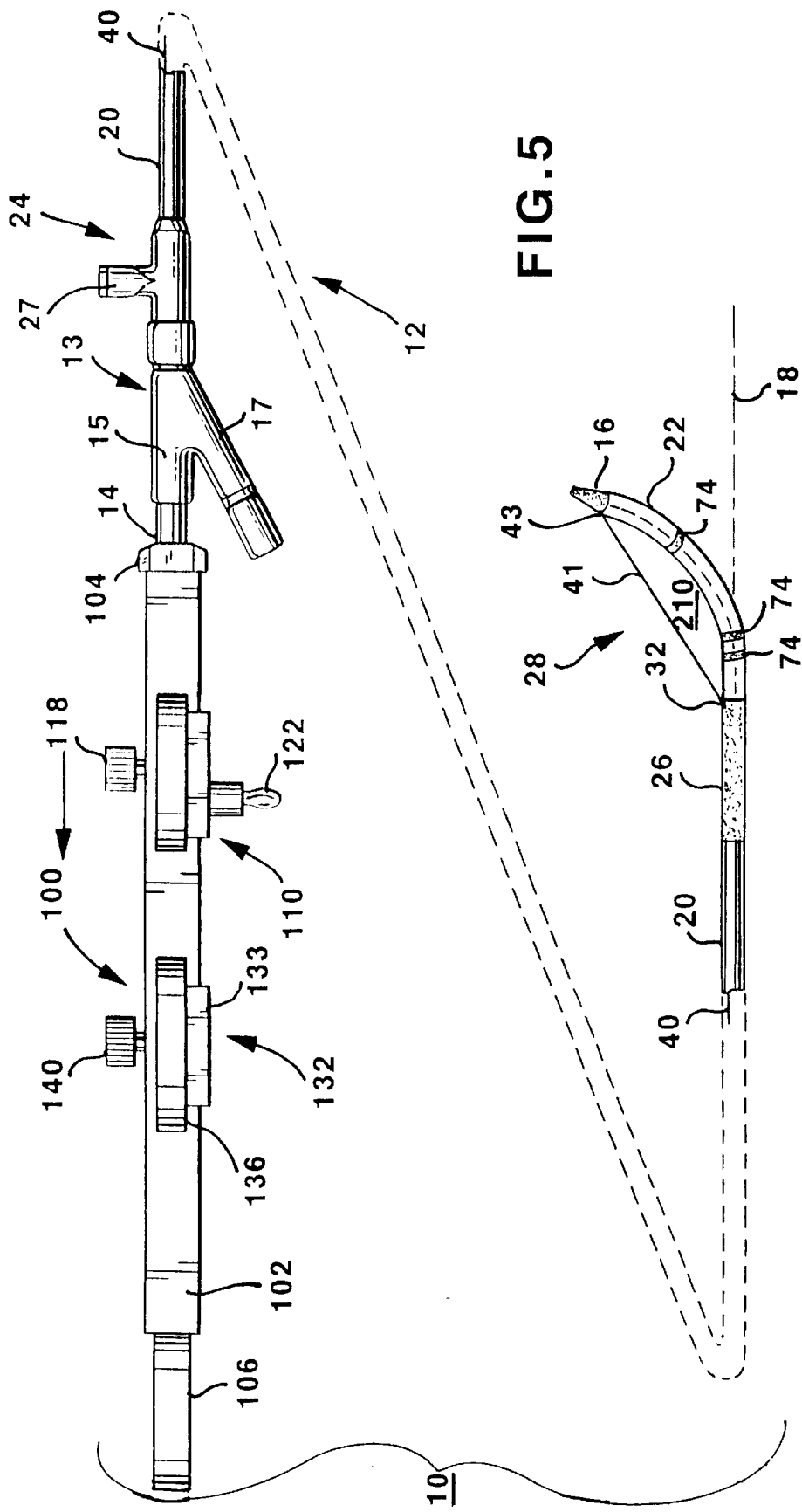
FIG. 5 is a side plan view of the sphincterotome of FIGS. 1–4 with the cutting wire partially retracted in the retracted position and forming a cutting plane with the distal end portion of the sphincterotome tubular member.
Figure 6:
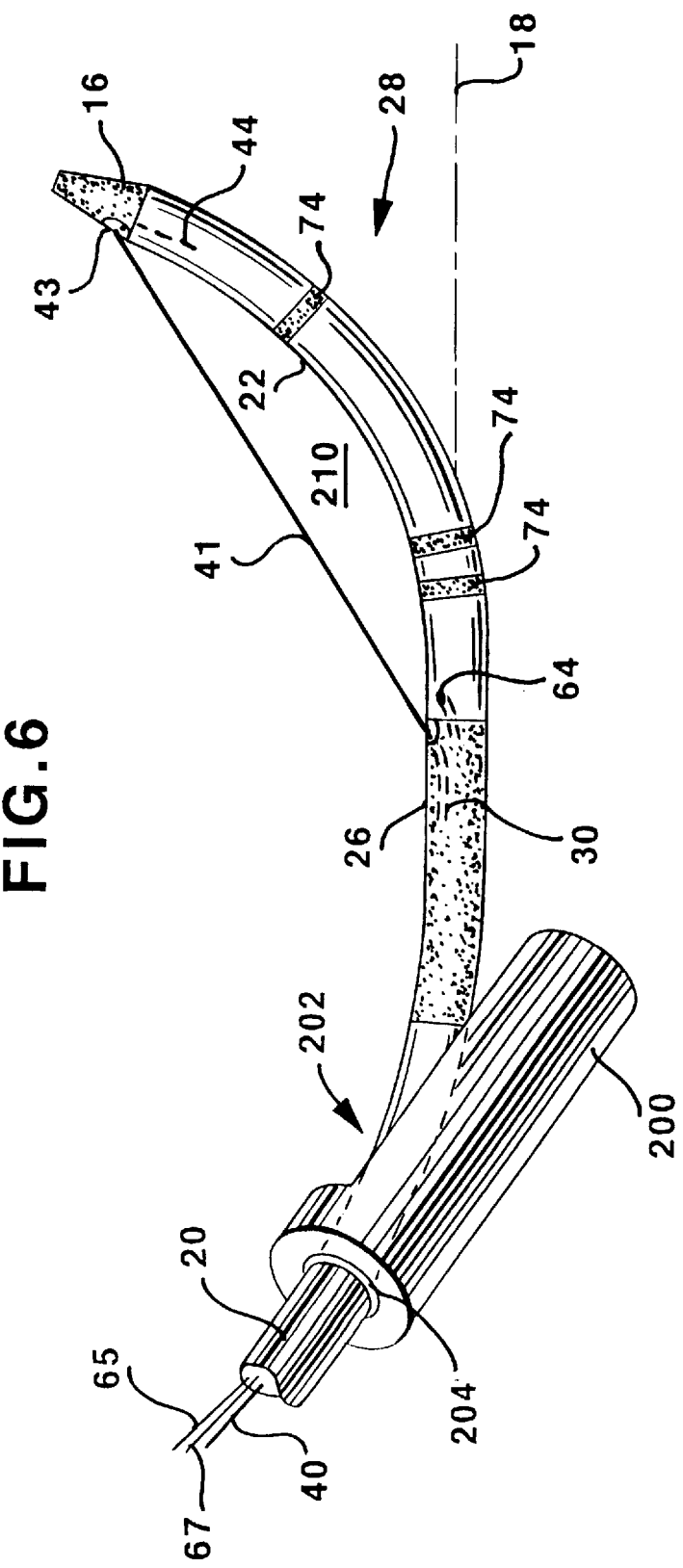
FIG. 6 is an enlarged partial side view of the distal end portion of the sphincterotome tubular member in the retracted position of FIG. 5 exiting the side exit opening of an endoscope.
Figure 7:
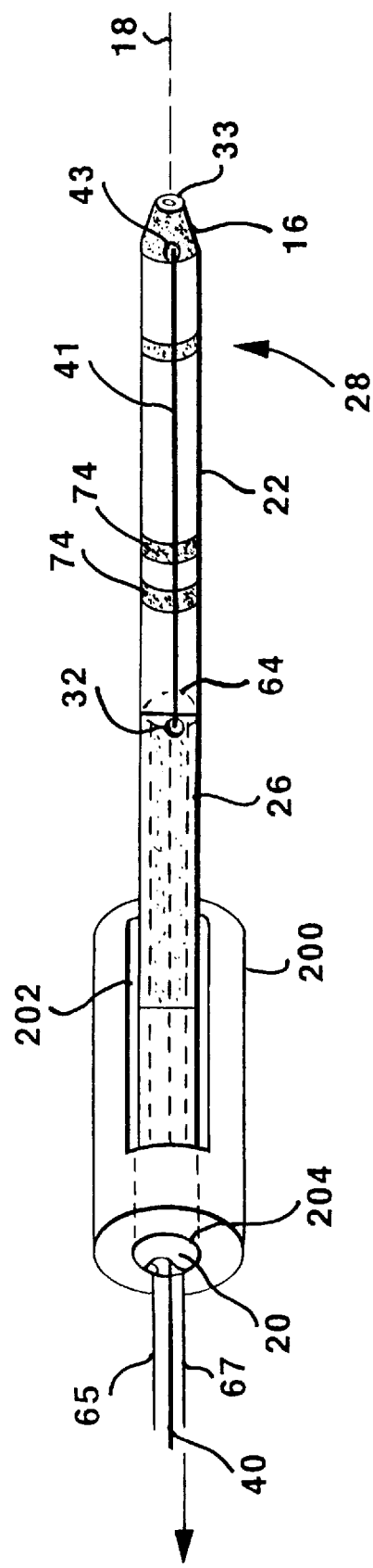
FIG. 7 is an enlarged partial top view of the distal end portion of the sphincterotome tubular member in the retracted position of FIG. 5 exiting the side exit opening of an endoscope.

Turning now to FIG. 5, it depicts a side view of the sphincterotome 10 with the distal section of the sphincterotome body 12 in an operative position having the cutting wire 40 retracted proximally through actuation of the cutting wire retracting and tensioning member 110 as described above to draw it toward the thumb engaging loop 106. FIGS. 6 and 7 depict the distal end segment 28 and cutting wire portion 41 exiting the endoscope side exit port 202 and forming a cutting plane 210. The tension exerted by the cutting wire retracting and tensioning member 110 on the distal, exposed cutting wire portion 41 separates it from the side wall 22 as it is retracted through side wall exit port 32. The bend is formed in the distal end segment 28, and the distal section forms the cutting plane 210 in the plane of the figure in a manner taught in the above-referenced '617 and '696 patents.

As in the ERS procedure described above, the distal tip of the endoscope 200 is initially placed at the site, and the sphincter opening is observed. The physician orients the side exit opening 204 at the best angle judged to be obtainable given the patient's anatomy. The tubular member 20 is inserted into the endoscope lumen 204 at the endoscope proximal end (not shown) to ensure that the exposed cutting wire portion 41 will be oriented to the proximal edge of the endoscope side exit opening 202 as it is advanced out from the endoscope side opening and toward the sphincter at a desired angle as shown in FIGS. 7 and 8 of the '617 patent.

In a first aspect of the invention, if it is necessary to do so, the method of practicing the invention may include the steps of manipulating the left and right pull wire tensioning and retracting members 130 and 132 to attain the desired orientation of the distal end section terminating in the distal tip 16 toward the sphincter opening with the exposed cutting wire portion 41 relatively slack alongside the distal end segment 28. In other words, either the left or right pull wire 65 or 67 may be retracted by retraction of the left and right finger engaging loops 134 and 136, respectively, causing a deflection of the distal end section to the left or right, respectively, with respect to the longitudinal axis 18 of the sphincterotome body, as viewed distally toward the distal tip 16. Thus, the physician may view the distal end section and the sphincter opening through the endoscope, apply and tension the appropriate pull wire to affect a lateral deflection to aim the distal tip into alignment with the sphincter opening while advancing the distal section into the opening. Then, the cutting plane 210 may be formed by retraction of the distal cutting wire portion 41 and the cutting plane 210 may be deflected as described below to orient the cutting plane 210 to a specific feature of the sphincter to allow the exposed and retracted cutting wire portion 41 to cut the sphincter when it is energized.

Continuing with the method of the present invention, and whether or not it is necessary to employ the method of the first aspect thereof, after placement of the distal end segment 28 and relaxed, exposed cutting wire portion 41 into the sphincter opening, the cutting wire retracting and tensioning member 110 is manipulated to retract the cutting wire 40 through the cutting wire lumen 30 and form the cutting plane 210. The alignment of the cutting plane 210 to the twelve o'clock position may be observed through the endoscope 200, and if it is mis-aligned toward the eleven o'clock position or the one o'clock position, the cutting plane may be shifted laterally with respect to the longitudinal axis of the sphincterotome tubular member 20 exiting the endoscope lumen to align the plane with the twelve o'clock position.

In accordance with this aspect of the present invention, the physician may apply right or left retraction force through manipulation of the pull wire tension and retracting members 132 and 130, respectively, to deflect the cutting plane 210 from the one o'clock and the eleven o'clock positions into alignment with the twelve o'clock position. The cutting plane 210 is maintained but deflected to the side about the axis of the sphincterotome tubular member 20 constrained within the endoscope side exit opening 202. While the tubular member 20 is itself not rotated, the deflection appears to be a rotary motion as viewed in an end view as described below. The deflection is within a limited range from the neutral position shown in FIGS. 5–8 to "fine tune" the actually achieved orientation.

It should be noted that the lateral deflection of the cutting plane 210 afforded by the present invention is characterized herein as a deflection and rotation with respect to the longitudinal axis of the tubular member 20 exiting the endoscope side opening. The movement may also include a slight rotation or twisting of the distal end segment resulting in the distortion of the planarity of the cutting plane 210 to a slight extent.

Figure 10:
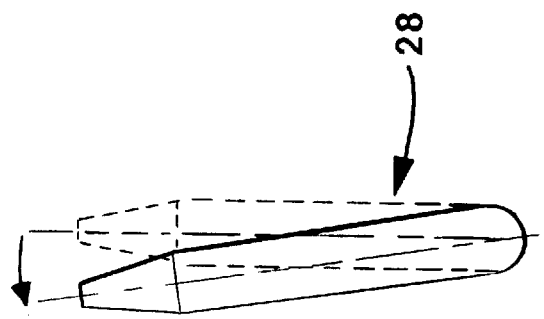
FIG. 10 is an idealized end view from lines 10—10 of FIG. 9 looking toward the endoscope opening showing the lateral deflection of the cutting plane achieved in FIG. 9.

Turning to FIGS. 8–10, the deflection of the cutting plane 210 to the left is illustrated. In FIG. 10, an idealized end view of the deflected distal segment 28 looking toward the endoscope lumen (not shown) illustrates the lateral deflection in a simplified manner (ignoring any lateral shift of the proximal portion of the distal end segment 28). The neutral position of the distal end segment 28 is shown in broken lines, and the clockwise deflection obtained in the manipulation of the left pull wire tension and retraction member 130 is shown in solid lines. The deflection of the entire cutting plane 210 is obtained because the left pull wire 65 terminates just distal to the side wall exit port 32, effectively applying lateral pulling force to one corner of the triangular cutting plane 210. The appearance of the deflection in FIG. 10 is of a clockwise motion (counterclockwise when viewed in the opposite direction from the endoscope 200) because of the constraint of the tubular body 20 afforded by the endoscope lumen and the tension on the cutting wire distal portion 41. Such a motion will correct for an orientation or deflection of the cutting plane 210 to the eleven o'clock position.

Figure 13:
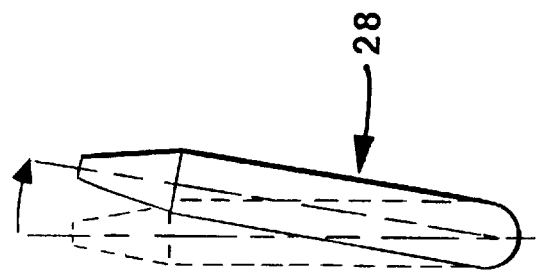
FIG. 13 is an idealized end view from lines 12—12 of FIG. 12 looking toward the endoscope opening and showing the deflection of the cutting plane achieved in FIG. 12.

The opposite result is attained by manipulation of the handle assembly as shown in FIGS. 11–13. The deflection to the right effected by pulling back on the right tension and retracting member 132 translates into a motion that will correct for an orientation of the cutting plane 210 to the one o'clock position.

In each case, the desired twelve o'clock position is attained by deflection through an angle of preferably between about +/−20° to +/−45° and less than 90° through manipulation of the finger engaging loop 134 or 136 to retract the associated pull wire 65 or 67 while observing the motion through the endoscope. The degree of lateral deflection can be visualized and controlled by the amount of tension and retraction applied to the pull wire. In this manner, the cutting plane 210 is oriented upon advancement of the distal end segment 28 and the distal cutting wire portion 41 from the endoscope side exit port 202 for selectively effecting lateral deflection of the cutting plane 210 with respect to the longitudinal axis 18 restrained by the endoscope lumen in at least one lateral direction through at least one angular range of less than 90° to orient the distal cutting wire portion into a selected cutting position.

Referring back to the first aspect of the invention, it will be understood that the distal end segment 28 may be deflected with the exposed cutting wire portion 41 relatively slack to assist in initially aligning advancing the distal end segment 28 and exposed cutting wire portion 41 into the sphincter opening as described above with respect to FIG. 4. This initial lateral deflection may be effected in the manner illustrated in FIGS. 8 and 11, but with the cutting wire retracting and tensioning member 110 remaining in the non-retracted position of FIGS. 1, 2 and 4. The resulting deflection of the distal end segment to the left and right of the longitudinal axis 18 (as viewed from the end of the endoscope 200) is also intended to be illustrated in FIGS. 9 and 12, assuming in this case that the distal end segment is relatively straight, i.e., not formed into the cutting plane 210.

Turning to further details of the construction of the sphincterotome of the present invention, as illustrated in FIG. 3, the pull wire lumens 62 and 63 are formed in the flexible tubular member laterally to first and second sides of the cutting wire lumen 30. The pull wire lumens 62 and 63 and the pull wires 65 and 67 extend from the proximal ends thereof through the tubular member 20 to respective pull wire attachment points that restrain the distal pull wire ends. Lateral deflection force is applied to the distal end section to laterally deflect the relatively straight and relaxed exposed cutting wire portion 41 and distal end segment 28 or the cutting plane 210 in the lateral directions illustrated in FIGS. 9–10 and 12–13 with respect to the longitudinal axis 18 in response to manipulation of the left and right pull wire retraction and tensioning members 130 and 132, respectively, to the tensioned positions of FIGS. 8 and 11, respectively. As shown in FIGS. 7, 9 and 11, the lumens 62 and 63 depicted in FIG. 3 are angled inward to a common pull wire termination site 64 just distal to the side wall exit port 32. The distal pull wire ends are preferably attached together at the common pull wire termination site 64, thereby forming a common pull wire attachment point. The joinder can be effected by adhesive bonding, brazing, soldering or other techniques. Preferably, a section cut is made in the tubular member 20 distal to the exit port 32 to access the distal pull wire ends without cutting the guidewire lumen 82. The pull wire distal ends are drawn out distally, brazed together, and pulled back into the section cut. The section cut and brazed together distal ends are sealed together with adhesive to form the termination site 64 and firmly hold the pull wire distal ends at the common attachment point.

While the invention has been described in particular reference to a sphincterotome for performing an ERS procedure of the type described above, it is reiterated that it may be used for similar sphincterotomy procedures of other sphincters or restricted passageways in the body. While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

What is claimed is:

1. A sphincterotome adapted to be introduced through an endoscope lumen and out an endoscope exit port into a sphincter opening to make a cut in alignment with a feature of a sphincter in a patient's body to enlarge the sphincter opening while avoiding endangering the patient, said sphincterotome comprising:

an elongated sphincterotome body having a proximal end and a distal end and a longitudinal axis extending therebetween, said sphincterotome body having a proximal end segment extending distally from said proximal end and a distal end segment extending distally from a junction with said proximal end segment to said distal end and further having a side wall dimensioned to be received in an endoscope lumen and having a predetermined length sufficient to allow the elongated sphincterotome body to be extended through said endoscope lumen to project at least said distal end segment thereof from said endoscope exit port and into proximity with the sphincter to be cut;

a cutting wire having an exposed cutting wire portion located alongside said distal end segment of said sphincterotome body;

means for supplying energy to said cutting wire to effect cutting of the patient's sphincter;

cutting plane defining means adapted to be operated when said distal end segment and said exposed cutting wire portion are extended from said endoscope exit port for selectively forming a bend in said distal end segment separating said exposed cutting wire portion from said side wall of said distal end segment to thereby form a cutting plane to enable cutting of the patient's sphincter upon energization of said cutting wire; and deflecting means selectively operable with operation of said cutting plane defining means for applying lateral deflection force to said cutting plane for laterally deflecting said cutting plane with respect to said longitudinal axis of said proximal end segment at said junction of said proximal end segment with said distal end segment to a deflected position of said cutting plane to orient said exposed cutting wire portion into a preferred planar angular alignment with said desired feature of the sphincter opening to facilitate cutting of the patient's sphincter by a cut made in the deflected cutting plane.

2. The sphincterotome of claim 1 further comprising:

a handle assembly coupled to said proximal end of said elongated sphincterotome body manipulatable by a user of the sphincterotome; and wherein said deflecting means further comprises:

means extending from said handle assembly to said junction of said proximal end segment and said distal end segment of said elongated sphincterotome body for applying lateral deflection force to said distal end segment after formation of said cutting plane by said cutting plane defining means to laterally deflect said cutting plane in at least one lateral direction with respect to said longitudinal axis in response to manipulation of said handle assembly.

3. The sphincterotome of claim 2 wherein said means extending from said handle assembly further comprises:

first means extending from said handle assembly to said junction of said proximal end segment and said distal end segment of said elongated sphincterotome body manipulatable by a user, after formation of said cutting plane by said cutting plane defining means, for applying lateral deflection force to said distal end in response to a first manipulation of said handle assembly to laterally deflect said cutting plane in at least a first lateral direction with respect to said longitudinal axis; and second means extending from said handle assembly to said junction of said proximal end segment and said distal end segment of said elongated sphincterotome body manipulatable by a user, after formation of said cutting plane by said cutting plane defining means, for applying lateral deflection force to said distal end segment in response to a second manipulation of said handle assembly to laterally deflect said cutting plane in a second lateral direction with respect to said longitudinal axis.

4. The sphincterotome of claim 3 wherein the deflection of said cutting plane in said first lateral direction and said second lateral direction from an un-deflected position aligned with said longitudinal axis, nominally characterized as 0°, encompasses a range of deflections of said cutting plane between about +20° to +45° with respect to 0° in said first lateral direction and between about −20° to −45° with respect to 0° in said second lateral direction.

5. The sphincterotome of claim 1 wherein:

said proximal end segment contains a cutting wire lumen extending from said proximal end through said proximal end segment to a side wall exit port at the junction of the proximal end segment with the distal end segment; and said cutting wire has a proximal cutting wire portion extending through said cutting wire lumen proximal to said exposed cutting wire portion exiting through said side wall exit port and extending alongside said side wall of said distal end segment and has a distal cutting wire end attached to said distal end segment adjacent said distal end of said sphincterotome body; and said cutting plane defining means further comprises cutting wire tensioning means coupled with said proximal cutting wire end and manipulatable to a slack position allowing said proximal cutting wire portion to be substantially slack within said cutting wire lumen and said exposed cutting wire portion to lie substantially slack alongside the side wall of said distal end segment during introduction through said endoscope lumen of said distal end segment and exposed cutting wire portion to a body site for performing a sphincterotomy, and manipulatable, upon advancement of said distal end segment and exposed cutting wire portion from said endoscope exit port, for partially retracting said exposed cutting wire portion into said side wall exit port and cutting wire lumen and forming a bend in said distal end segment separating said exposed cutting wire portion from said side wall of said distal end segment to thereby form said cutting plane.

6. The sphincterotome of claim 5 wherein said deflecting means further comprises:

a first pull wire lumen formed in said elongated sphincterotome body and extending from said proximal end to a first pull wire attachment point adjacent said junction of said proximal end segment with said distal end segment;

a first pull wire having a first pull wire proximal end and a first pull wire distal end extending through said first pull wire lumen;

first pull wire tensioning means at the proximal end of said sphincterotome body coupled with said first pull wire proximal end and manipulatable between a slack position for allowing said first pull wire to be slack within said first pull wire lumen and a tensioned position for retracting said first pull wire through said first pull wire lumen; and first means for restraining said first pull wire end at said first pull wire attachment point for applying lateral deflection force to said distal end segment to laterally deflect said distal end segment and said distal exposed cutting wire portion in a first lateral direction with respect to said longitudinal axis in response to manipulation of said first pull wire tensioning means to a tensioned position effecting retraction of said first pull wire.

7. The sphincterotome of claim 6 wherein said first pull wire lumen is formed in said elongated sphincterotome body extending in parallel with and laterally offset from said longitudinal axis and along a first side of said cutting wire lumen and from said proximal end to said pull wire attachment point at said junction of said proximal end segment with said distal end segment.

8. The sphincterotome of claim 6 wherein said deflecting means further comprises:

a second pull wire lumen formed in said elongated sphincterotome body extending from said proximal end to a second pull wire attachment point adjacent said junction of said proximal end segment with said distal end segment;

a second pull wire having a second pull wire proximal end and a second pull wire distal end extending through said second pull wire lumen;

second pull wire tensioning means at the proximal end of said sphincterotome body coupled with the second pull wire proximal end and manipulatable between a slack position for allowing said second pull wire to be slack within said second pull wire lumen and a tensioned position for retracting said second pull wire through said second pull wire lumen; and second means for restraining said second pull wire distal end at said second pull wire attachment point for applying lateral deflection force to said distal end segment to laterally deflect said distal end segment and said distal exposed cutting wire portion in a second lateral direction with respect to said longitudinal axis in response to manipulation of said second pull wire tensioning means to a tensioned position effecting retraction of said second pull wire.

9. The sphincterotome of claim 8 wherein said first pull wire tensioning means and said second pull wire tensioning means are operable, following tensioning of said cutting wire by operation of said cutting wire tensioning means to form said cutting plane, to selectively retract said first pull wire within said first pull wire lumen and said second pull wire within said second pull wire lumen, respectively, and effect the deflection of said cutting plane from an un-deflected position aligned with said longitudinal axis, nominally characterized as 0°, in said first and second lateral directions, respectively, and into a deflected position within a range of deflections of said cutting plane between about +20° to +45° with respect to 0° in said first lateral direction and between about −20° to −45° with respect to 0° in said second lateral direction.

10. The sphincterotome of claim 8 wherein:
said first pull wire lumen is formed in said elongated sphincterotome body extending in parallel with and laterally offset from said longitudinal axis and along a first side of said cutting wire lumen and from said proximal end to said first pull wire attachment point at said junction of said proximal end segment with said distal end segment; and
said second pull wire lumen is formed in said elongated sphincterotome body extending in parallel with and laterally offset from said longitudinal axis and along a second side of said cutting wire lumen and from said proximal end to said second pull wire attachment point at said junction of said proximal end segment with said distal end segment.

11. The sphincterotome of claim 10 wherein:
said first pull wire lumen and said second pull wire lumen extend to a common attachment point comprising said first attachment point and said second attachment point; and
said first pull wire distal end and said second pull wire distal end are joined to one another at said common attachment point.

12. The sphincterotome of claim 10 wherein said first pull wire tensioning means and said second pull wire tensioning means are operable, following tensioning of said cutting wire by operation of said cutting wire tensioning means to form said cutting plane, to selectively retract one of said first and second pull wires and effect the deflection of said cutting plane from an un-deflected position aligned with said longitudinal axis, nominally characterized as 0°, in said first and second lateral directions, respectively, and into a deflected position within a range of deflections of said cutting plane between about +20° to +45 with respect to 0° in said first lateral direction and between about −20° to −45° with respect to 0° in said second lateral direction.

13. The sphincterotome of claim 1 wherein said lateral deflecting means is operable to effect a lateral deflection from an un-deflected position aligned with said longitudinal axis and into a deflected position within a range of deflections of between about 20° to 45° with respect to said longitudinal axis.

14. The sphincterotome of claim 1 wherein said deflecting means is selectively operable from said proximal end for deflecting said distal end segment and said exposed cutting wire portion extending from said endoscope exit port laterally with respect to said longitudinal axis to orient said distal end of said sphincterotome body into axial alignment with the sphincter opening to facilitate advancement of said distal end segment and said cutting wire axially into the sphincter opening before said cutting plane forming means is manipulated to form said cutting plane.

15. A sphincterotome adapted to be advanced through the lumen of an endoscope and out an endoscope exit port into a sphincter opening of a sphincter in a patient's body to make a cut in alignment with a feature of the sphincter to enlarge the sphincter opening while avoiding endangering the patient, of the type comprising:
an elongated sphincterotome body extending between a proximal end and a distal end formed of an elongated generally tubular, flexible tubular member having a proximal end segment extending distally from said proximal end and a distal end segment extending distally from a junction with said proximal end segment to said distal end, said flexible tubular member with a side wall dimensioned to fit within and be constrained by the endoscope lumen during advancement through the endoscope lumen, the flexible tubular member having an elongated axis extending between said proximal end and said distal end, and a flexible tubular member length sufficient to allow the flexible tubular member to be extended through said endoscope lumen to project at least said distal end segment thereof from said endoscope exit port and into proximity with the sphincter to be cut, said distal end segment being normally substantially straight and having a bending flexibility allowing a bend to be formed therein, said flexible tubular member containing a cutting wire lumen extending from said proximal end through said proximal end segment to a side wall exit port through said side wall at the junction of the proximal end segment with the distal end segment and first and second pull wire lumens extending through said flexible member length between a distal pull wire attachment point in said flexible tubular member proximal to said distal end and said proximal end of said sphincterotome body, said pull wire lumens being oriented within an arc of less than 180° with respect to said longitudinal axis;
a sphincterotome cutting wire having a proximal cutting wire end, a proximal cutting wire portion extending through said cutting wire lumen, an exposed cutting wire portion exiting through said side wall exit port and extending alongside said side wall of said distal end segment, and a distal cutting wire attached to said distal end segment adjacent said distal end of said sphincterotome body;
first and second pull wires, extending within said first and second pull wire lumens, respectively, between said distal attachment point and said proximal end of said sphincterotome body; and
a handle assembly at the proximal end of said sphincterotome body further comprising:
cutting wire tensioning means coupled with said proximal cutting wire end and manipulatable to a slack position allowing said proximal cutting wire portion to be substantially slack within said cutting wire lumen and said exposed cutting wire portion to lie substantially slack alongside the side wall of said distal end segment during introduction of said distal end segment and exposed cutting wire portion to a body site through said endoscope lumen for performing a sphincterotomy, and manipulatable, upon advancement of said distal end segment and exposed cutting wire portion from said endoscope exit port, within a range of operative positions for partially retracting said exposed cutting wire portion into said side wall port and cutting wire lumen and forming a bend in said distal end segment separating said exposed cutting wire portion from said side wall of said distal end segment in a cutting plane for performing a sphincterotomy, said cutting plane defined by the retracted, exposed cutting wire portion and the bent distal end segment; and
first and second pull wire tensioning means operable upon advancement of said distal end segment and said exposed cutting wire portion from said endoscope exit port and retraction of said exposed cutting wire port to form said cutting plane for selectively retracting one of said first and said second pull wires, respectively, through said first and said second respective pull wire lumens, and thereby applying a first or a second laterally displaced tension along a first or a second side of said distal end segment, respectively, effecting angular deflection of said cutting plane formed by said distal end segment and exposed cutting wire portion with respect to said longitudinal axis restrained by said endoscope lumen through respective first and second angular ranges of between about 25° to 40° deflection from said longitudinal axis to orient said exposed cutting wire portion into a preferred planar angular alignment with a desired feature of the sphincter opening to facilitate cutting of the patient's sphincter.

16. The sphincterotome of claim 15 wherein:

said first pull wire lumen is formed in said flexible tubular member laterally to a first side of said cutting wire lumen and extends from said proximal end to said distal pull wire attachment point at said junction of said proximal end segment with said distal end segment; and said second pull wire lumen is formed in said elongated sphincterotome body laterally to a second side of said cutting wire lumen and extends from said proximal end to said distal pull wire attachment point at said junction of said proximal end segment with said distal end segment.

17. The sphincterotome of claim 16 wherein:

said distal ends of said pull wire and said further pull wire are joined to one another at said distal pull wire attachment point.

18. The sphincterotome of claim 16 wherein said first pull wire tensioning means and said second pull wire tensioning means are operable, following tensioning of said cutting wire by operation of said cutting wire tensioning means to form said cutting plane, to selectively retract one of said first and second pull wires and effect the deflection of said cutting plane from an un-deflected position aligned with said longitudinal axis, nominally characterized as 0°, into a deflected position within a range of deflections of said cutting plane between about +20° to +45° with respect to 0° in a first lateral direction and between about −20° to −45° with respect to 0° in a second lateral direction.

19. A method of surgically making a cut in alignment with a feature of a patient's sphincter to enlarge the sphincter opening while avoiding endangering the patient, comprising the steps of:

providing a sphincterotome comprising:

an elongated sphincterotome body having a proximal end and a distal end and a longitudinal axis extending therebetween, said sphincterotome body having a proximal end segment extending distally from said proximal end and a distal end segment extending distally from a junction with said proximal end segment to said distal end, said sphincterotome body further having a side wall dimensioned to be received in an endoscope lumen and having a predetermined length sufficient to allow the elongated sphincterotome body to be extended through said endoscope lumen to project at least a distal end segment thereof from said endoscope exit port and into proximity with the sphincter to be cut;

a cutting wire having an exposed cutting wire portion located alongside said distal end segment of said sphincterotome body;

means for supplying energy to said cutting wire to effect cutting of the patient's sphincter;

deflecting means selectively operable from said proximal end for deflecting said distal end segment and said exposed cutting wire portion extending from said endoscope exit port laterally with respect to said longitudinal axis; and cutting plane defining means for selectively forming said distal end segment and said exposed cutting wire portion extending from said endoscope exit port into a cutting plane to enable cutting of the patient's sphincter;

positioning an endoscope having an endoscope lumen terminating in an endoscope exit port near the sphincter to allow viewing of the sphincter and sphincter opening;

extending said sphincterotome body through said endoscope lumen to project at least said distal end segment of said sphincterotome body and said exposed cutting wire portion out of said endoscope exit port and adjacent the sphincter opening;

advancing at least a portion of said distal end segment and exposed cutting wire portion projecting out of said sphincterotome exit port into said sphincter opening;

operating said cutting plane defining means to form said cutting plane to allow said exposed cutting wire portion to cut said sphincter when energized;

operating said deflecting means to deflect said cutting plane with respect to said longitudinal axis to effect a desired planar angular alignment of said cutting plane with respect to a feature of the sphincter opening to facilitate cutting of the patient's sphincter by a cut made in the deflected cutting plane; and energizing said exposed cutting wire portion to effect cutting of said sphincter.

20. The method of claim 19, wherein the step of operating said deflecting means to deflect said cutting plane further comprises the step of:

operating said deflecting means to deflect said cutting plane in a range of deflections of between about 20° to 45° and less than 90° with respect to said longitudinal axis to orient said cutting plane into a desired angular alignment with a feature of said sphincter opening.

21. The method of claim 19 further comprising the step of:

operating said deflecting means to deflect said distal end segment and exposed cutting wire portion with respect to said longitudinal axis and to orient said distal end into alignment with said sphincter opening to facilitate the step of advancing at least a portion of said distal end segment and exposed cutting wire portion into said sphincter opening before forming said cutting plane.

22. A sphincterotome adapted to be advanced through an endoscope lumen and out an endoscope exit port for cutting a sphincter in a patient's body to enlarge the sphincter opening while avoiding endangering the patient, said sphincterotome comprising:

an elongated sphincterotome body having a proximal end and a distal end and a longitudinal axis extending therebetween, said sphincterotome body having a proximal end segment extending distally from said proximal end and a distal end segment extending distally from a junction with said proximal end segment to said distal end, said sphincterotome body further having a side wall dimensioned to be received in an endoscope lumen and having a predetermined length sufficient to allow the elongated sphincterotome body to be extended through said endoscope lumen to project at least a distal end segment thereof from said endoscope exit port and into proximity with the sphincter to be cut said sphincterotome body containing a cutting wire lumen extending from said proximal end through said proximal end segment to a side wall exit port through said side wall at the junction of the proximal end segment with the distal end segment;

a cutting wire extending through said cutting wire lumen of the elongated sphincterotome body from the proximal end thereof and through said cutting wire exit port and alongside a distal end segment of said sphincterotome body to an attachment to said distal end;

cutting plane forming means coupled with the proximal end of the sphincterotome body adapted to be manipulated after the distal end segment of the sphincterotome body is extended through said endoscope lumen and out the endoscope exit port to retract said cutting wire and said exposed cutting wire portion through said cutting wire lumen and exit port and to thereby form a cutting plane as a bend is induced in the distal end segment by the retraction of the exposed cutting wire portion, the cutting plane extending away from and in axial alignment with a longitudinal axis of the proximal end segment of the sphincterotome body restrained in the endoscope lumen, said cutting plane defined by the retracted, exposed cutting wire portion and the bent distal end segment; and deflecting means coupled with the proximal end of the sphincterotome body and extending through the length of said proximal end segment of said sphincterotome body to an attachment point with said distal end segment in proximity with said cutting wire exit port for deflecting the cutting plane laterally with respect to the longitudinal axis of the sphincterotome body exiting the endoscope exit port to a deflected position of said cutting plane to orient said exposed cutting wire portion into a preferred planar angular alignment with said desired feature of the sphincter opening to facilitate cutting of the patient's sphincter.

23. The sphincterotome of claim 22 wherein said deflecting means is selectively operable from said proximal end for deflecting said distal end segment and said exposed cutting wire portion extending from said endoscope exit port laterally with respect to said longitudinal axis to orient said distal end of said sphincterotome body into axial alignment with the sphincter opening to facilitate advancement of said distal end segment and said cutting wire axially into the sphincter opening before said cutting plane forming means is manipulated to form said cutting plane.

* * * * *